Nov. 23, 1954 T. E. MOTOSE Plant Pat. 1,323
ROSE PLANT
Filed Nov. 25, 1953
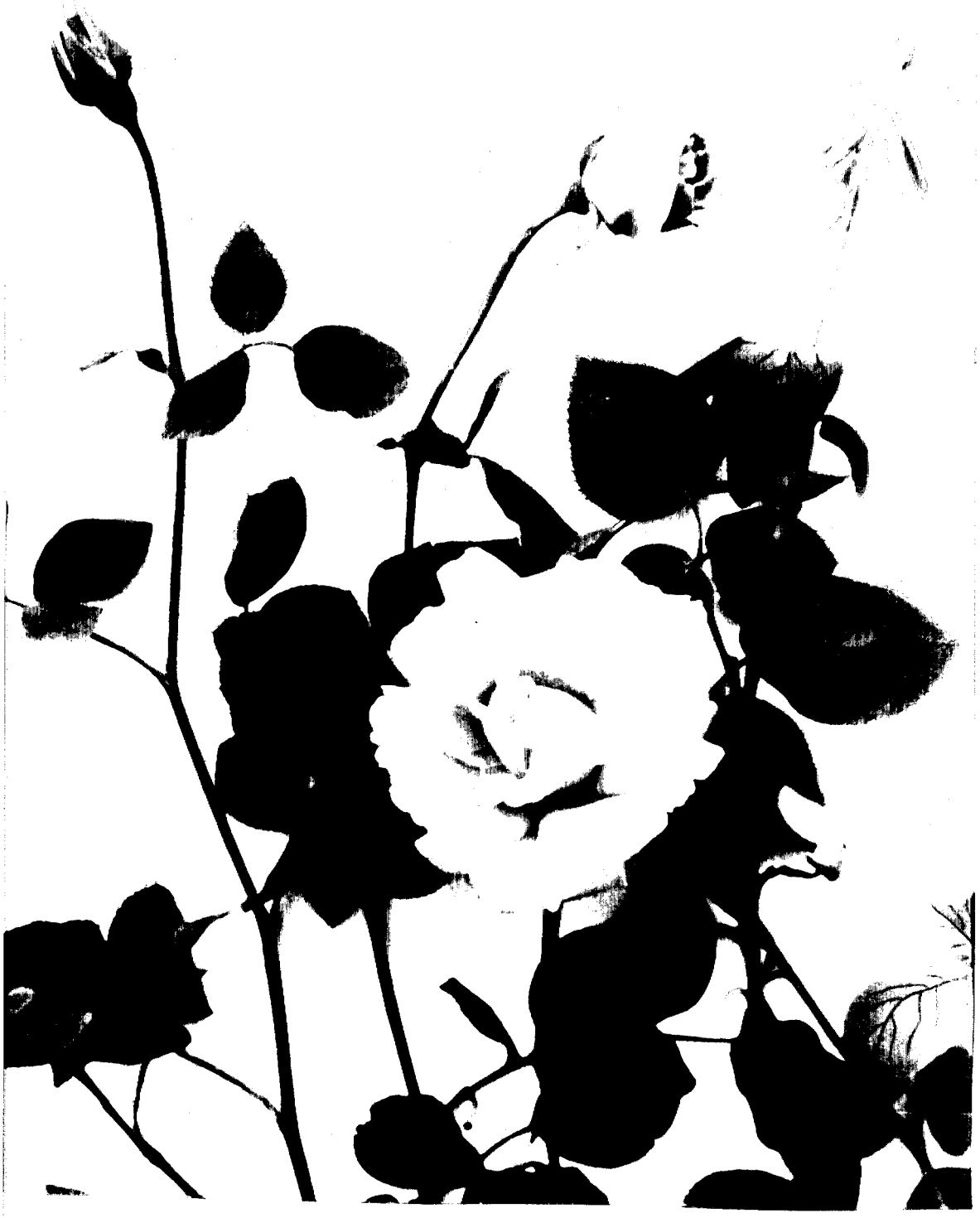
Inventor
Thomas Edison Motose United States Patent Office Plant Pat. 1,323

Patented Nov. 23, 1954

1,323

ROSE PLANT

Thomas Edison Motose, Fairport, N. Y.

Application November 25, 1953, Serial No. 394,527

1 Claim. (Cl. 47—61)

The present invention relates to a new and distinct variety of hybrid tea rose, originating from a cross-pollination between a sport of the known hybrid tea variety La France and a seedling which was a cross between the known hybrid tea varieties Senator and Florex. (None of the parent roses are patented.) Its object was to secure a variety of hybrid tea rose having the following characteristics: (*a*) thornless branches; (*b*) very sweet fragrance other than the delicious odor of tea; (*c*) moderately full or pleasantly double blossom, but not too many petals as to make the bloom appear grotesque or freakish; (*d*) branches, leaves and buds possessing smoothness and grace, rather than toughness and coarseness; (*e*) great production of blooms on long stems; (*f*) recurrent, continuous bloooming habit; (*g*) tendency to flourish in greenhouse or underglass culture; (*h*) and ability to compete with other hybrid tea roses in outdoor sunlight.

A sport found by me on La France was used as the seed-parent because it was very fragrant and had very few thorns. The seedling obtained from a cross between Senator and Florex was used as the pollen parent because it also had very few thorns and had many of the qualities sought for. Both parents were unsatisfactory by themselves because they had thorns, although few in number. However, by repeated crossings of the two roses, I finally obtained a new variety of hybrid tea rose possessing the qualities I have been looking for.

This new hybrid tea rose is characterized as to novelty by the combination of the following traits or characteristics: (*a*) thornless branches; (*b*) great production of blooms on medium and long stems suitable for cut-flower trade and greenhouse production; (*c*) tendency to produce a high percentage of "one to a stem" blooms; (*d*) fine, smooth texture and deep rose-pink petals; (*e*) delicate petals with "ruffled-like" outer edges which are frequently marked with beautiful indentations; (*f*) sweet, "old-rose" like fragrance, long lasting and tending to permeate its surroundings; (*g*) unusually long, continuous blooming habit; (*h*) and moderately double (which may be described as "pleasingly" double) blossoms, but not with too many petals as to make the flowers appear freakish, grotesque or massive.

The above characteristics and traits, particularly the thornless branches and continuous blooming habit, have been found to hold true through succeeding asexual propagations by the usual methods of cuttings, graftings and buddings, and are established.

The accompanying pictures illustrate the leaves, stems, branches, buds, flowers and other parts of this new hybrid tea rose; and the colorings appearing thereon were those prevailing at the time and place (early September, Fairport, N. Y.) the pictures were made.

This new rose plant reproduces faithfully the general basic rose-pink color in its blooms, but the degree or intensity of that color undergoes minor changes with the changes in temperature, location, soil condition and the intensity and length of sun-light. This new rose plant will reproduce faithfully the basic green color in its leaves and stems, but the degree or intensity of that color will also undergo minor changes with the changes in temperature, soil condition and solar exposure; and cannot be defined with, named by, or "nailed-down" to, any split hair nomenclature or specific plate number of any known color standard. The degree, depth or intensity of the rose-pinkness of its bloom, and the degree, depth or intensity of the greenness of its leaf and stem are not, by themselves, the distinguishing factors in this invention. The rose-pink color of the bloom, in combination with the characteristics named hereinabove and to be described in detail in the paragraphs to follow, becomes one of the distinguishing factors of this new variety of rose plant.

The color terminology (without specific plate number) herein employed is in accordance with standard meaning of Webster's Dictionary of the English Language; the color comparisons herein given are with those of well-known plants; and the color terminology with specific plate number given herein is in accordance with Ridgway's Color Standards and Nomenclature.

The place where, and time when, observations made for the specific purpose compiling data on the colors of the various parts of the new rose plant for this specification: Early in September 1953, in Fairport, N. Y., greenhouses.

The place where, and the duration of, observations made for the specific purpose of compiling data on the various characteristics, other than the colors, of the new variety of rose plant: Shrub Oak, N. Y., and Fairport, N. Y., beginning from the time of germination to maturity of the plant, through countless asexual propagations, and indoors and outdoors tests.

The following is a detailed description of the new variety of rose plant, the subject of this application:

(*a*) *Parentage.*—A seedling resulting from a cross-pollination between a sport of La France (seed parent) and a seedling which was a cross of Senator and Florex.

(*b*) *Botanic classification.*—Hybrid-tea rose.

(*c*) *Commercial classification.*—Greenhouse type hybrid tea rose.

(*d*) *Place where asexually reproduced.*—Shrub Oak, N. Y., and Fairport, N. Y.

(*e*) *Method of asexual reproduction.*—Budding, cutting and grafting.

(*f*) *Flowering habit.*—Its habit is recurrent, continuous; abundant flowers in greenhouse.

(*g*) *Flower-bud.*—Its size before calyx breaks is medium; its form is roundish at the base and pointed at the top; its color as the calyx breaks is rose-pink where the petal shows; its size as the first petal opens is between medium and large; its color as the first petal opens is deep Rose-Pink (Plate XII), except at the petal's base where the deep rose pink color gently merges into a pinkish white color comparable to the general coloring of a newly opened blossom of a standard strain of Baldwin apple; its sepals, not branched as a rule, curl back partly when petals begin to unfurl; its peduncle is medium to long, medium heavy, erect stiff, medium green and has occasional soft green hairs thereon.

(*h*) *Opening.*—The buds open very well.

(*i*) *Flower.*—Its size when full opened is four to five inches; its petalage is double and full, ranging from 20 to 35 petals depending upon the season and soil condition; it form as the first few petals open is "high center" and gradually becoming "open center" as it ages; its color is Deep Rose Pink (Plate No. XII), reverse and obverse, when newly opened, except toward the base of petals where the Deep Rose Pink gradually merges into a light pinkish white color comparable to the hue of a newly opened blossom of a standard strain of Baldwin apple; its tonality at the end of first day of bloom is Deep Rose Pink (Plate No. XII), at the end of second day of bloom Deep Rose Pink (Plate No. XII), at the end of third day of bloom Rose Pink (Plate No. XII) and at the end of fourth day of bloom La France Pink (Plate No. I); its fragrance is very sweet resembling that of *Rosa centifolia,* but with an individuality or peculiarity of its own; its normal habit is to bloom "one to a stem," and rarely in multiple; and its lasting quality on the plant and as cut-flower is long and very good.

(*j*) *Petal.*—Its texture is soft, delicate and medium thin; its general form is "heart" shape with the base pointed but not sharp and the top more rounded; its outer edges are frequently indented and appear artistically ruffled; its appearance on the reverse side is satiny and the obverse side partly silky; its persistence on growing stem is determined by temperature, humidity and season—sometimes drops off cleanly and sometimes clings; its persistence as "cut-flower" is very good and clingy.

(*k*) *Genital organs.*—Its anthers are medium in size, many in number, Light Orange Yellow (Plate No. III) in color and regular in arrangement; its filaments are long in length, regular in arrangement and pale yellow in color; its pollen is moderate in quantity, Light Orange Yellow (Plate No. III) in color; its styles are separate but arranged closely as to give a columnar appearance, medium in height, pale yellow in color; its stigma is medium in size and Morocco Red (Plate No. I) on the upper sides and edges, and Martius Yellow (Plate No. IV) around the orifice; and its ovaries are mostly enclosed in the calyx.

(*l*) *Foliage.*—Its formation is a compound of five leaflets as a general rule, but occasionally three and rarely seven; its size is medium; its appearance is "slightly" wrinkled, with ribs and veins well marked; its leaflet is ovate-rotundate in general shape with the apex slightly pointed but not sharp and the base rounded; its color when the leaflets are partly closed or starting to unfurl in greenhouse is Yellowish Oil Green (Plate No. V) with slight bronze, and sometimes reddish, tinge on the visible parts; its colors when the young leaflets have fully unfurled themselves in greenhouse are Deep Dull Yellow Green (Plate No. XXXII) with slight bronze tinge on the upper side and Yellowish Oil Green (Plate No. V) with slight bronze tinge on the under side; its colors when one or two weeks old in greenhouse are variable from Apple Green (Plate No. XVII) to Parrot Green (Plate No. VI) on the upper surface and Calliste Green (Plate No. VI) on the under surface; its colors when mature (in its prime) in greenhouse are Deep Grape Green (Plate No. XLI) on the upper surface and Bice Green (Plate No. XVII) on under surface; its colors at old age in greenhouse, but before senile discolorations start, are Lincoln Green (Plate No. XLI) on the upper surface and Hellebore Green (Plate No. XVII) on the under surface; its texture is slightly leathery on both sides; its edges are serrated and the serration is small, not too sharp and occasionally double; and its stipules are medium length and comparatively smooth.

(*m*) *Wood.*—Its size is medium; its color when few months old is Deep Grape Green (Plate No. XLI) and when older a Lincoln Green (Plate XLI); and its bark is very smooth.

(*n*) *Thorns.*—It has no thorns on all its natural and normal branches and stems at all seasons.

(*o*) *Plant as a whole.*—Its form is bushy; its length is that of the average hybrid tea rose plant; its growth is free, vigorous and well branched; its hardiness and disease resistance are similar to those of its parents and related roses without any special weakness or susceptibility.

(*p*) *Asexual reproduction.* — Countless tests have shown that the differentiating characteristics and traits of this new variety of rose plant, especially the thornless branches, the recurrent and continuous blooming quality and the tendency to produce an exceedingly high percentage of "one to a stem" blooms, are thoroughly established and hold true through succeeding asexual propagations. But the seeds from this new variety, like those from any other hybrid stock, will not always reproduce the same characteristics; and any branch of this new variety that has undergone any appreciable degree of mutation, like any other sport on any hybrid tea rose plant, may produce thorns and other characteristics totally absent in the parent stock and its normal asexual descendants.

I claim:

A new and distinct variety of hybrid tea rose plant characterized as to novelty and usefulness by the combination of its thornless branches, its smooth bark, its rose-pink colored bloom with frequent appearance of delicate dentations and ruffled-like edges on the petals, its great production of blooms under greenhouse culture, its tendency to produce exceedingly large number of blooms of the type known as "one to a stem" and particularly suitable for cut-flower trade, its recurrent or continuous blooming ability or habit in direct and in filtered sunlights, together with its foliage characteristics, substantially as shown and described.

No references cited.